United States Patent [19]

Hellenkamp

[11] 4,038,571

[45] July 26, 1977

[54] PIEZOELECTRIC DENTAL CLEANING DEVICE

[75] Inventor: Johann F. Hellenkamp, Miami, Fla.

[73] Assignee: Litton Industrial Products, Inc., Beverly Hills, Calif.

[21] Appl. No.: 430,504

[22] Filed: Jan. 3, 1974

[51] Int. Cl.² .............................................. H01L 41/04
[52] U.S. Cl. ....................................... 310/8.2; 310/8.3
[58] Field of Search .................. 310/8.1, 8.2, 8.3, 8.7, 310/26; 318/116, 118; 32/DIG. 4, 58; 128/24 A

[56] References Cited

U.S. PATENT DOCUMENTS

| 3,368,280 | 2/1968 | Friedman et al. | 32/58 |
| 3,427,480 | 2/1969 | Robinson | 310/8.1 |
| 3,518,766 | 7/1970 | Burt | 310/8.1 X |
| 3,809,977 | 5/1974 | Balamuth et al. | 310/8.1 X |
| 3,934,526 | 1/1976 | DaMast et al. | 310/8.3 X |
| 3,993,425 | 7/1971 | Robinson | 32/58 |

Primary Examiner—Mark O. Budd
Attorney, Agent, or Firm—W. R. Thiel

[57] ABSTRACT

This device uses a piezoelectric crystal for converting electrical energy into mechanical vibrations which are transmitted to a dental workpiece for use in cleaning teeth. The device includes a front cap having flats which engage flats on the tip base attached to the dental workpiece and allows dental workpieces to be interchanged. The device includes a tie rod disposed within the tubular crystal around which water circulates between the tie rod and the tubular crystal. Axial bores allow passage of the water to the tip of the workpiece to wash away debris on the teeth during cleaning.

10 Claims, 3 Drawing Figures

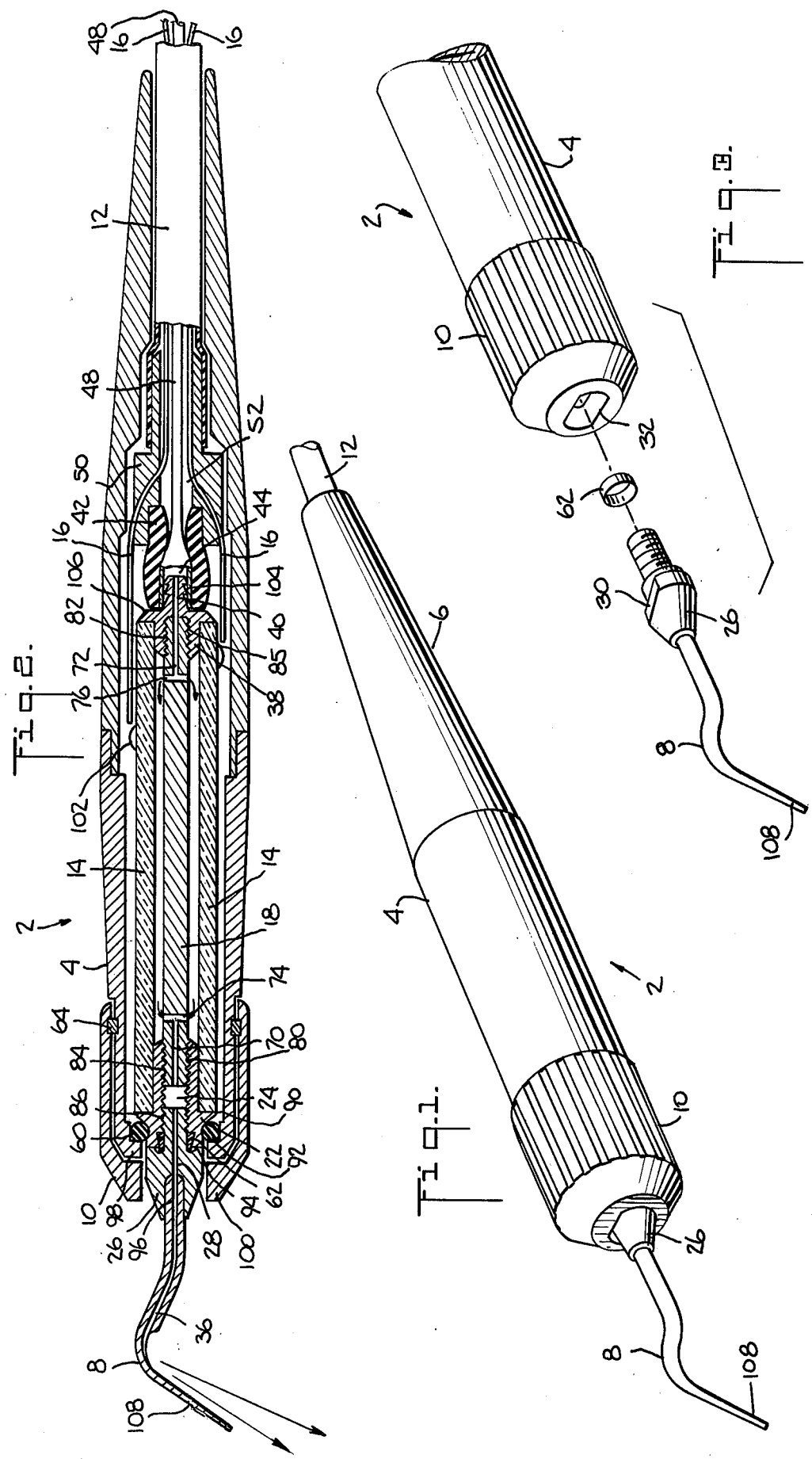

PIEZOELECTRIC DENTAL CLEANING DEVICE

BACKGROUND OF THE INVENTION

1. Field of the Invention

The field of this invention relates to dental cleaning devices and more particularly to devices using a piezoelectric crystal to convert electrical energy into mechanical vibrations and transmit such vibrations to a dental workpiece for cleaning teeth.

2. Description of the Prior Art

Although piezoelectric dental cleaning devices are known in the prior art, none have the novel design and resulting advantages of the device disclosed herein.

Prior art piezoelectric dental cleaning devices include those disclosed in the following U.S. Pat Nos.: 3,645,255 and 3,427,480 to Robinson; 3,526,036 to Goof; 3,518,766 to Burt; and 3,368,280 to Friedman et al.

Other patents of interest include the following U.S. Pat. Nos.: 2,874,470 to Richards; 3,075,288 and 3,213,537 to Balamuth et al.; 3,124,878 to Bodine, Jr. et al.; 3,133,351 to Von Seggern; 3,076,904 to Kleesattel et al.; 2,792,674 to Balamuth et al.; and 2,990,616 to Balamuth et al.

SUMMARY OF THE INVENTION

This invention relates to a piezoelectric dental cleaning device which uses ultrasonic vibrations for cleaning the teeth, that is for, dislodging debris from teeth including tartar, stain, loose particles, calculi, etc. In general, the device uses a dental workpiece mechanically coupled to a piezoelectric crystal to form a compound ultrasonic resonator.

The piezoelectric dental cleaning device of this invention includes a hollow, tubular, piezoelectric crystal and electric wires to provide electrical energy to the crystal; a tie rod axially disposed within the crystal; an acoustical transformer attached to the front portion of the tie rod and to the front portion of the crystal; a tip base connected to the front portion of the acoustical transformer; a dental workpiece mounted in the front portion of the tip base; a fluid connector attached to the rear portion of the tie rod; a silicone rubber bumper connected to the rear portion of the fluid connector; a fluid tube connected to the rear portion of the bumper and to the rear portion of the fluid connector; a wire holder connected to the bumper and to the fluid tube; an outer case which houses the foregoing components of this device; and a front cap. The front cap is rotatably positioned around the front portion of the outer case and the front cap has interior flats which are dimensioned to engage external flats on the tip base to tighten or loosen or facilitate removal of the tip base and dental workpiece.

A major object and feature of this invention is to provide a piezoelectric dental cleaning device of novel design to allow convenient interchangeability of dental workpieces. This is accomplished in this invention by the front cap which acts as a wrench on the tip base to tighten or loosen or remove the tip base and workpiece from the dental cleaning device.

Another major object and feature of this invention is to provide a piezoelectric dental cleaning device of simple design which can be easily and economically manufactured and which provides improved operational efficiency and durability.

Another object and feature of this invention is to provide a lightweight ultrasonic cleaning device for dental use in which the vibrations are directly transmitted to the tip, thereby reducing undesirable reviberatory vibrations.

Other objects and features of this invention will become apparent from the drawings and the following detailed description.

DESCRIPTION OF THE DRAWINGS

FIG. 1 is an isometric view of the piezoelectric dental cleaning device of this invention.

FIG. 2 is a longitudinal sectional view of FIG. 1.

FIG. 3 is an exploded view of part of the piezoelectric dental cleaning device shown in FIG. 1 for the purpose of showing how the dental workpiece may be removed from the device.

DETAILED DESCRIPTION

Referring to FIG. 1, the piezoelectric dental cleaning device of this invention is designated generally by the numeral 2 and includes an outer case which is composed of a front portion 4 and a rear portion 6. The dental workpiece 8 is positioned at the front end of the dental cleaning device 2 and may be removed by rotation of the front cap 10 which is positioned around the front end of the front portion 4 of the outer case. Electrical energy and fluid are supplied to the dental cleaning device 2 through a coaxial tube 12.

Referring to FIG. 2, the piezoelectric dental cleaning device 2 includes a hollow, tubular piezoelectric crystal 14 for converting electrical energy into mechnical vibrations. The crystal 14 has a front portion and a rear portion. Electrical wires 16 are electrically connected to the crystal 14 to provide electrical energy to the crystal 14. A tie rod 18 is axially disposed within the tubular crystal 14. The tie rod has a front portion and a rear portion and is designed with means, which shall be described in greater detail subsequently, to allow the passage of fluid from the rear portion of the tie rod 18 to the front portion of the tie rod 18. A acoustical transformer 22 is attached to the front portion of the tie rod 18 and to the front portion of the piezoelectric crystal 14. The acoustical transformer 22 has an axial bore 24. The rear portion of tip base 26 is connected to the front portion of the acoustical transformer 22. The tip base 26 has an axial bore 28 to allow the passage of fluid.

Referring to FIG. 3, the tip base 26 has exterior flats 30 on a portion of its outer circumference. The flats 30 on the tip base 26 are dimensioned to engage interior flats 32 at the front end of cap 10. The engagement of flats 32 and 30 enables the cap 10 to act as a wrench on tip base 26 as cap 10 is rotated about the front portion 4 of the outer case. Thereby, cap 10 is adapted to tighten or loosen or facilitate the removal of tip base 26 and workpiece 8 from the piezoelectric dental cleaning device 2.

Returning to FIG. 2, the dental workpiece 8 is mounted in the front portion of tip base 26 and the dental workpiece 8 has an axial bore 36 to allow the passage of fluid. The workpiece 8 is made preferably of metal, such as a stainless steel, beryllium copper, or other suitable material, in the form of an elongated rod terminating in an appropriately shaped working tip 108. Such tips 108 vary in specific shape according to the dental function required. As a result, it is important that the workpiece 8 be interchangeable within dental cleaning device 2 with other workpieces 8. The workpiece 8 is permanently affixed to tip base 26 and is interchangeable as a result of the novel design of this invention which includes the flats 30 on tip base 26, the flats 32 within the interior flange 100 of front cap 10 and the wrench-like action of front cap 10. This novel design enables the user to change dental workpieces 8 quickly, efficiently and conveniently.

A fluid connector 38 is attached to the rear portion of tie rod 18 and the fluid connector 38 has an axial bore 40 to permit the passage of fluid. A silicone rubber bumper 42 is connected to the rear portion of the fluid connector 38. Bumper 42 has an irregular cylindrical shape and has an axial bore 44. The front portion of the fluid tube 48 has an enlarged diameter adapted to fit over the rear portion of fluid connector 38. Fluid connector 38 has an irregular cylindrical shape and the exterior diameter of the rear portion of fluid connector 38 is slightly smaller than the interior diameter of the front portion of fluid tube 48. The rear portion of fluid connector 38 has recesses 104 which engage and grip the fluid tube 48. Fluid connector 38 also has an annular exterior collar 106 which abuts against the rear portion of crystal 14 and against the front portion of bumper 42.

The front portion of fluid tube 48 passes through the axial bore of bumper 42 and the fluid tube 48 has an axial bore to permit the passage of fluid. A wire holder 50 is also attached to the rear portion of bumper 42 and the wire holder 50 has an axial bore 52 through which the fluid tube 48 is disposed. Electrical wires 16 pass through wire holder 50 and are held in place thereby.

A coating 102 of silver or other conductive metal may be provided to fuse the electrical wires 16 to the outer diameter of crystal 14. A conductive epoxy cement may also be used. The fluid tube 48 should be made of a non-conductive material such as silicone rubber. The axial bore 40 of fluid connector 38 aligns with the rear axial bore 72 of tie rod 18 to allow the passage of fluid from fluid tube 48 through axial bore 40 of fluid connector 38 through the rear axial bore 72 of tie rod 18.

An O ring 60 is mounted around the transducer 22 and between the acoustical transformer 22 and the front end of the front portion 4 of the outer case. A washer-like teflon seal 62 is positioned around a portion of the tip base 26 between the tip base 26 and the acoustical transformer 22. A snap ring 64 is positioned within the front cap 10 at the rear portion of the front cap 10 and between the front cap 10 and the front portion 4 of the outer case. An annular groove may be provided on the outer surface of the front portion 4 of the outer case and on the inner surface of front cap 10 to receive snap ring 64 and thereby facilitate the rotation of front cap 10 with respect to the front portion 4 of the outer case.

Referring to FIG. 2, the means, previously referred to, to allow the passage of fluid from the rear portion of the tie rod 18 to the front portion of the tie rod 18 includes a front axial bore 70 at the front end of the tie rod 18 extending partially through the tie rod 18 longitudinally and a rear axial bore 72 at the rear end of the tie rod 18 extending partially through the tie rod 18 longitudinally. A front radial bore 74 extends through the circumference of the tie rod 18 and the front radial bore 74 is positioned at the interior termination point of the front axial bore 70, thereby establishing communication between the front axial bore 70 and the front radial bore 74. A rear radial bore 76 extends through the circumference of the tie rod 18 and the rear radial bore 76 is positioned at the interior termination point of the rear axial bore 72, thereby establishing communication between the rear axial bore 72 and the rear radial bore 76. Thus, the front radial bore 74 is positioned at right angles to the front axial bore 70 and the rear radial bore 76 is positioned at right angles to the rear axial bore 72. As a result of bores 70, 72, 74 and 76, passage of fluid is permitted through the rear axial bore 72, then through rear radial bore 76, then around the outer circumference of tie rod 18 between tie rod 18 and piezoelectric crystal 14, then through the front radial bore 74 and then through front axial bore 70. The passage of fluid between tie rod 18 and piezoelectric crystal 14 has the effect of cooling piezoelectric crystal 14. In this embodiment, the fluid used is water, although other fluids may also be used. In this embodiment, the plane of the front radial bore 74 of tie rod 18 is perpendicular to the plane of the rear radial bore 76 of tie rod 18.

Still referring to FIG. 2, tie rod 18 has exterior screw threads 80 on the outer circumference of the front portion of tie rod 18 and exterior screw theads 82 on the outer circumference of the rear portion of tie rod 18. Acoustical transformer 22 has interior screw threads 84 along the axial bore 24 of acoustical transformer 22. Portions of interior screw threads 84 at the rear portion of acoustical transformer 22 are adapted to engage the screw threads 80 at the front portion of tie rod 18. The fluid connector 38 has interior screw threads 84 at the front portion of the fluid connector 38 and these internal screw threads 84 are adapted to engage the screw threads 82 at the rear portion of tie rod 18.

The tip base 26 has exterior screw threads 86 at the rear portion of the tip base 26 around the outer circumference of the tip base 26. These exterior screw threads 86 of tip base 26 are adapted to engage portions of the interior screw threads 84 at the front portion of acoustical transformer 22 to connect the rear portion of the tip base 26 to the front portion of the acoustical transformer 22. The action of rotating front cap 10 causes tip base 26 to rotate as a result of the engagement of flats 30 and 32, shown in FIG. 3. When tip base 26 rotates, it rotates with respect to acoustical transformer 22, shown in FIG. 2, by means of screw threads 84 and 86. These screw threads 84 and 86 allow the tip base 26 and workpiece 8 to be tightened or loosened or removed with respect to the dental cleaning device 2, as shown in FIG. 3.

In the embodiment shown in FIG. 2, the tubular piezoelectric crystal 14, which is mounted internally within the outer casing 4 and 6, is a lead zirconate-lead titanate ceramic crystal 14. The crystal 14 is capable of ultrasonic vibrational activity in its longitudinal direction when activated by high frequency electrical impulses delivered to it by electrical wires 16. The crystal 14 is of smaller outer diameter than the interior diameter of outer case 4 and 6 and the crystal 14 is supported coaxially by acoustical transformer 22 and fluid connector 38. The crystal 14 is firmly attached by means of a waterproof seal to acoustical transfomer 22 and fluid connector 38. In this embodiment, the waterproof seal is produced by use of epoxy cement between inerior wall at the rear portion of crystal 14 and water connector 38 and between interior wall at the front portion of crystal 14 and acoustical transformer 22.

The acoustical transformer 22 has an irregular cylindrical shape. The rear portion of acoustical transformer 22 has an exterior diameter which is slightly smaller than the interior diameter of the front portion of tubular crystal 14 so that the rear portion of acoustical transformer 22 will fit within the front portion of the tubular crystal 14. The acoustical transformer 22 has an annular exterior shoulder 90 against which the front end of crystal 14 abuts. The front portion of acoustical transformer 22 has a neck 92. Neck 92 of acoustical transformer 22 has a diameter which is slightly smaller than the diameter of O ring 60 so that O ring 60 fits around neck 92. Optionally, an annular groove may be provided in neck 92 for O ring 60.

Tip base 26 is an irregular cylinder, the rear portion of which has a diameter slightly smaller than the axial bore 24 of acoustical transformer 22 so that the exterior screw threads 86 at the rear of tip base 26 may engage interior screw threads 84 of acoustical transformer 22. Tip base 26 has an annular shoulder 94 against which the front end of acoustical transformer 22 abuts. Tip base 26 has an interior well 96 in the tapered front end of tip base 26. The rear portion of dental workpiece 8 is press fit and silver soldered into well 96 of tip base 26. For this purpose, the rear portion of dental workpiece 8 is dimensioned to have a slightly smaller diameter than the diameter of well 96. The front axial bore 70 of tie rod 18 aligns and communicates with the axial bore 24 of acoustical transformer 22, with the axial bore 28 of tip base and with the axial bore 36 of dental workpiece 8 to allow the passage of fluid therethrough.

The outer case 4 and 6 is an irregular cylinder. The front portion 4 of the outer case has, at its front end, an interior flange 98 which maintains the position of O ring 60 with reference to shoulder 90 of acoustical transformer 22.

The front cap 10 is an irregular cylinder having an interior flange 100 at the front end of cap 10. The interior diameter of interior flange 100 is slightly larger than the largest exterior diameter of tip base 26 to allow tip base 26 to pass within and through interior flange 100 and to facilitate engagement of the flats 32 located on the interior flange 100 of front cap 10 with the flats 30 on the exterior diameter of tip base 26, as shown in FIG. 3. In this embodiment tip base 26 has two flats 30 and front cap 10 has two corresponding flats 32. Other embodiments may be designed with a larger number of flats.

The dental cleaning device 2 is connected to a supply of fluid and to oscillatory electric power supply by means of fluid tube 48 and electric wires 16 within coaxial tube 12. In this embodiment, the fluid tube 48 is connected to a water supply (not shown) and wires 16 are connected to a conventional oscillator (not shown) whose output and frequency may by varied as desired. The oscillating power delivered from the oscillator will provide the desired piezoelectric effect in ultrasonic vibrations from piezoelectric crystal 14 to workpiece 8. For example, at an operating frequency of about 28,900 c.p.s., the applied voltage to the piezoelectric crystal 14 would be in the range of about 53 to 200 volts (R.F.), 40 watts at desired voltage. One wire 16 is preferably connected to the hot side of the oscillator and the other wire 16 is connected to the neutral side for protection against possible shock.

To provide for a fluid outlet and to direct a pressure jet stream of fluid, such as water, to the tip 108 of workpiece 8 adjacent to the region of the dental surface being worked upon for removal of debris thereat by such fluid strain, the workpiece 8 is provided with an axial bore 36. The crystal 14 expands and contracts in a longitudinal direction when excited by the high frequency electrical oscillations. While such crystals may be designed to produce this effect with oscillations from 20,000 c.p.s. to 45,000 c.p.s., preferably for dental application the response should not exceed 35,000 c.p.s. Each crystal 14 is designed to respond more or less to a specific frequency and the replaceable workpiece 8 provides a compound resonator responsive to the selected frequency. The following table describes the properties of piezoelectric crystals suitable for use with this invention:

|  | Crystal 1 (strontium additive) | Crystal 2 (niobium additive) |
| --- | --- | --- |
| Coupling coefficients: |  |  |
| $K_p$ | .59 | .64 |
| $K_{33}$ | .66 | .70 |
| $K_{31}$ | .34 | .35 |
| Piezoelectric Constants: |  |  |
| $D_{33}$ (meters per volt) | $284 \times 10^{-12}$ | $375 \times 10^{-12}$ |
| $D_{31}$ (meters per volt) | $-120 \times 10^{-12}$ | $-170 \times 10^{-12}$ |
| $G_{33}$ (volt-meters per Newton) | $25\ 10^{-3}$ | $24\ 10^{-3}$ |
| $G_{31}$ (volt-meters per Newton) | $-11 \times 10^{-3}$ | $-11.5 \times 10^{-3}$ |
| Dielectric Constant, $K_3$ | 1,300 | 1,700 |
| Frequency Constants: |  |  |
| Radial (cycle-meters per second) | 2,100 | 2,000 |
| Thickness (cycle-meters per second) | 1,950 | 1,800 |
| Elastic Constants: |  |  |
| $YE_{11}$ (gm./cm. $^2$) | $8.2 \times 10^{-10}$ | $6.1 \times 10^{-10}$ |
| $YE_{33}$ (gm./cm. $^2$) | $6.6 \times 10^{-10}$ | $5.3^1 \times 10^{-10}$ |
| Density (gm./cm. $^3$) | 7.6 | 7.6 |
| Mechanical Q | 600 | 65 |
| Curie Point (° C.) | 325 | 365 |

The crystal 14 can be electrically energized to have vibratory components in other than the longitudinal direction to provide various effects at the tip, as desired. This can be accomplished by changing the excitation frequency. In addition, the location of applying the voltage to the crystal 14 can be varied to produce different effects. For example, by applying the voltage across opposite ends of the crystal 14, a torsional effect is produced. The front portion 4, of the outer case, the rear portion 6 of the outer case, the front cap 10 and the wire holder 50 may all be molded of a synthetic resinous composition, such as "Lexan" which is a registered U.S. Trademark No. 637,022 in the name of General Electric Company, Schenectady, New York. The tip base 26, tie rod 18 and fluid connector 38 may be made of a non-corrosive metal, such as stainless steel.

What is claimed is:
1. A piezoelectric dental cleaning device comprising:
   a. a hollow, tubular, piezoelectric crystal for converting electrical energy into mechanical vibrations, said crystal having a front portion and a rear portion;
   b. electric wires electrically connected to said crystal to provide electrical energy to said crystal;
   c. a tie rod axially disposed within said tubular crystal, said tie rod having a front portion and a rear portion, said tie rod having means to allow the passage of fluid from the rear portion of said tie rod to the front portion of said tie rod;
   d. a acoustical transformer having a front portion and a rear portion, said rear portion of said acoustical transformer being attached to the front portion of said tie rod and to the front portion of said crystal, said acoustical transformer having an axial bore;
   e. a tip base having a front portion and a rear portion, said rear portion of the tip base being connected to the front portion of said acoustical transformer, said tip base having an axial bore to allow the passage of fluid and flats on a portion of the outer circumference of said tip base;

f. a dental workpiece, having a front portion and a rear portion, said rear portion of the dental workpiece being mounted in the front portion of said tip base, said workpiece having an axial bore to allow the passage of fluid;

g. a fluid connector having a front portion and a rear portion, the front portion of said fluid connector being attached to the rear portion of said tie rod and to the rear portion of said crystal, said fluid connector having an axial bore to permit the passage of fluid;

h. a bumper having a front portion and a rear portion, said front portion of the bumper being connected to the rear portion of said fluid connector, said bumper having an axial bore;

i. a fluid tube having a front portion and a rear portion, said front portion of the fluid tube being connected to the rear portion of said bumper, said fluid tube having an axial bore to permit the passage of fluid;

j. a wire holder having a front portion and a rear portion, the front portion of said wire holder being attached to the rear portion of said bumper, said wire holder having an axial bore within which the fluid tube is disposed;

k. an outer case which houses th crystal, tie rod, acoustical transformer, tip base, fluid connector, bumper, wire holder, fluid tube and electric wires; and l. a front cap having a front portion and a rear portion and a substantially cylindrical configuration, the interior circumference of said cap being slightly larger than the outer circumference of the front portion of said outer case, said cap being rotatably positioned around the front portion of said outer case, said cap having interior flats at the front end of said cap, said flats being dimensioned to engage the flats on the exterior of said tip base to tighten or loosen or facilitate the removal of tip base and workpiece.

2. A piezoelectric dental cleaning device according to claim 1, and further comprising:

a. an O ring mounted around said acoustical transformer and between said acoustical transformer and the front portion of said outer case;

b. a washer-like seal positioned around the tip base and between the tip base and the acoustical transformer; and c. a snap ring positioned within the front cap at the rear portion of the front cap and between the front cap and the outer case.

3. A piezoelectric dental cleaning device according to claim 1, wherein said means to allow the passage of fluid from the rear portion of said tie rod to the front portion of said tie rod comprises:

a. a front axial bore at the front end of said tie rod extending partially through said tie rod;

b. a rear axial bore at the rear end of said tie rod, extending partially through said tie rod;

c. a front radial bore extending through the circumference of said tie rod, said front radial bore being positioned at the interior termination point of said front axial bore;

d. a rear radial bore extending through the circumference of said tie rod, said rear radial bore being positioned at the interior termination point of said rear axial bore;

whereby said front radial bore is positioned at right angles to said front axial bore, said rear radial bore is positioned at right angles to said rear axial bore and whereby said bores permit the passage of fluid through said rear axial bore, then through said rear radial bore, then around the outer circumference of said tie rod between said tie rod and said piezoelectric crystal, then through said front radial bore, and then through said front axial bore.

4. A piezoelectric dental cleaning device according to claim 3, wherein the plane of said front radial bore of tie rod is perpendicular to the plane of said rear radial bore of said tie rod.

5. A piezoelectric dental cleaning device according to claim 1, wherein:

a. said tie rod has screw threads on the outer circumference of the front portion of said tie rod and screw threads on the outer circumference of the rear portion of said tie rod;

b. said acoustical transformer has interior screw threads along the axial bore of said acoustical transformer, said interior threads at the rear portion of said acoustical transformer being adapted to engage the screw threads at the front end of said tie rod; and c. said fluid connector has interior screw threads at the front portion of said fluid connector, said internal screw threads of said fluid connector being adapted to engage the screw threads at the rear portion of said tie rod;

d. said tip base has exterior screw threads at the rear portion of said tip base around the outer circumference of said tip base, said screw threads being adapted to engage the interior screw threads at the front portion of said acoustical transformer to connect the rear portion of said tip base to the front portion of said acoustical transformer.

6. A piezoelectric dental cleaning device according to claim 1, wherein said piezoelectric crystal is firmly attached by means of a waterproof seal to said acoustical transformer and said fluid connector.

7. A piezoelectric dental cleaning service according to claim 2, wherein said acoustical transformer has an irregular cylindrical shape, the rear portion of said acoustical transformer having an exterior diameter which is slightly smaller than the interior diameter of the front portion of said tubular crystal whereby the rear portion of said acoustical transformer fits within the front portion of said tubular crystal, said acoustical transformer having an annular exterior shoulder against which the front end of said crystal abuts, the front portion of said acoustical transformer having a neck the diameter of which is slightly smaller than the diameter of said O ring whereby said O ring fits around said neck, and said acoustical transformer having an axial bore, said axial bore having interior screw threads.

8. A piezoelectric dental cleaning device according to claim 7, wherin said tip base has an irregular cylindrical shape, the rear portion of said tip base having a diameter slightly smaller than said axial bore of said acoustical transformer, said tip base having exterior screw threads at the rear portion of said tip base adapted to engage interior screw threads of said acoustical transformer, said tip base having an annular shoulder against which the front end of said acoustical transformer abuts, and said tip base having an interior well in the front end of said tip base adapted to receive the rear portion of said dental workpiece.

9. A piezoelectric dental cleaning device according to claim 1, wherein said front cap has an irregular cylindrical shape, said cap having an interior flange at the front end of said cap, the interior diameter of said interior flange being slightly larger than the largest exterior diameter of said tip base to allow said tip base to pass within and through said interior flange of said front cap, said interior flange having flats adapted to engage flats on the exterior diameter of said tip base.

10. A piezoelectric dental cleaning device according to claim 1, wherein said fluid connector has an irregular cylindrical shape, the rear portion of said fluid connector having an exterior diameter which is slightly smaller than the interior diameter of the front portion of said fluid tube, the rear portion of said fluid connector having exterior recesses which engage and grip the front portion of said fluid tube, said fluid connector also having an annular exterior collar which abuts against the rear portion of said crystal and against the front portion of said bumper.

* * * * *